United States Patent [19]

Ichikawa

[11] Patent Number: 4,737,912

[45] Date of Patent: Apr. 12, 1988

[54] MEDICAL IMAGE FILING APPARATUS

[75] Inventor: Kaori Ichikawa, Koganei, Japan

[73] Assignee: Olympus Optical Co., Ltd., Japan

[21] Appl. No.: 771,894

[22] Filed: Sep. 3, 1985

[30] Foreign Application Priority Data

Sep. 21, 1984 [JP] Japan .................. 59-196540

[51] Int. Cl.$^4$ ............................ G06F 15/40
[52] U.S. Cl. ....................... 364/413; 430/952; 430/356
[58] Field of Search ............... 358/342; 364/413, 200; 430/952, 356

[56] References Cited

U.S. PATENT DOCUMENTS

| | | | |
|---|---|---|---|
| 3,970,996 | 7/1976 | Yasaka | 364/900 |
| 4,485,454 | 11/1984 | Kimoto | 364/900 |
| 4,553,206 | 11/1985 | Smutek | 364/300 |
| 4,572,891 | 2/1986 | Drexler | 346/76 L |
| 4,587,635 | 5/1986 | Hashimoto | 358/342 |

Primary Examiner—Jerry Smith
Assistant Examiner—Gail O. Hayes
Attorney, Agent, or Firm—Parkhurst & Oliff

[57] ABSTRACT

In a medical image filing apparatus having a store unit, a keyboard, a retrieval device, a display unit and a CPU, case images of various diseases are stored in the store unit together with clinical images, and case indexes corresponding to respective case images and clinical indexes corresponding to respective clinical images are also stored in the store unit. Therefore, the retrieval operation of the case images as well as the clinical images can be effected in an easy and swift manner, and thus it is possible to effect an accurate diagnosis for a patient.

9 Claims, 2 Drawing Sheets

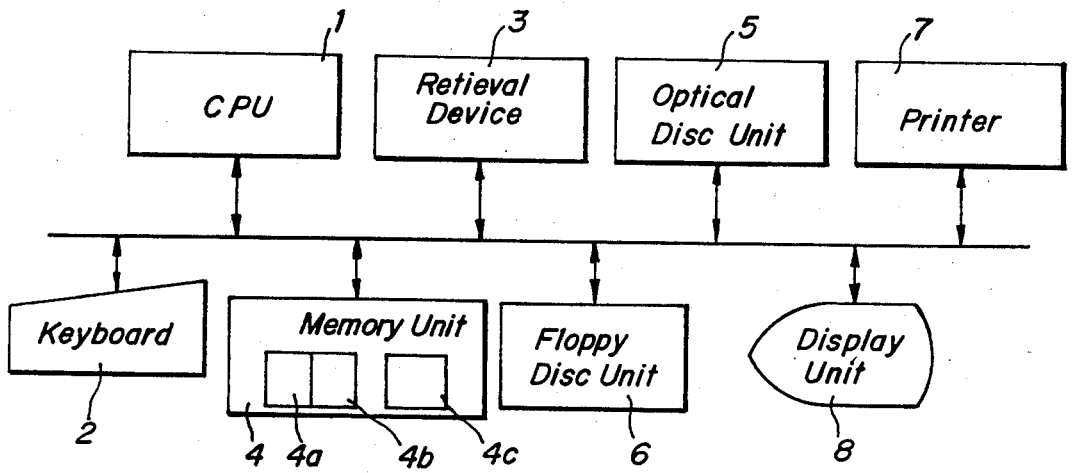

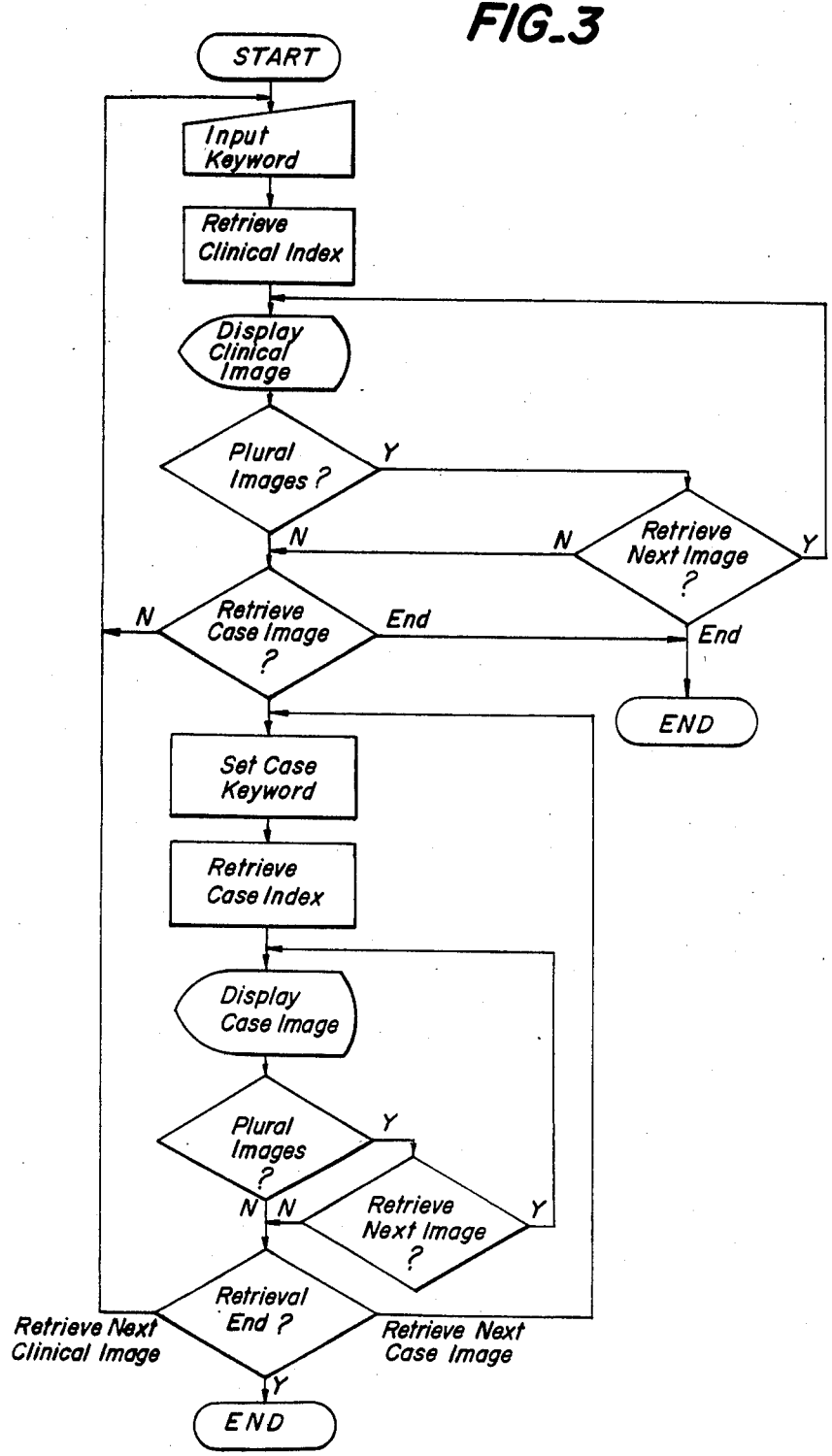

MEDICAL IMAGE FILING APPARATUS

BACKGROUND OF THE INVENTION

Field of the Invention and Related Art Statement

The present invention relates to a medical image filing apparatus.

Recently, as to a medical treatment system, there has been proposed an image filing system in which clinical images such as endoscope images, X-ray images, microscope images of pathological specimens, etc. of various patients are filed under the control of a computer, and such an image filing system has been used for a diagnosis and a management of case histories. In the medical image filing apparatus mentioned above, many clinical images taken in clinical diagnoses are recorded together with indexes having address data representing filing positions of the images in a record medium and retrieval data including a plurality of keywords such as name of patient, sex distinction, birthday, date of diagnosis, name of disease, part of disease, name of doctor in charge, etc. When retrieval data is inputted from a keyboard, the recorded clinical images are collated with the retrieval data and one or more clinical images having retrieval data identical with the inputted retrieval data are retrieved and are successively displayed on a display unit.

Further, when the doctor diagnoses a patient with reference to his clinical images, it is sometimes necessary to see one or more case images of related disease for reference in order to perform an accurate diagnosis. However, in the known medical image filing apparatus, only the clinical images taken by the actual diagnoses are recorded on the record medium, and the case images or reference images of diseases are not recorded. In this case, there occurs the drawback that it is necessary to find necessary case images from a great number of case images described on books.

SUMMARY OF THE INVENTION

The present invention has for its object to eliminate the drawbacks mentioned above and to propose a medical image filing apparatus by means of which one can easily and swiftly observe case images as well as clinical images.

According to the invention, a medical image filing apparatus comprises means for storing case images, clinical images taken in clinical diagnoses, case indexes including retrieval data of said case images, and clinical indexes including retrieval data of said clinical images;

means for inputting retrieval data corresponding to desired case image and clinical image;

means for retrieving at least one image corresponding to said inputted retrieval data out of all the images stored in said storing means;

means for displaying retrieved images; and means for controlling said storing means, inputting means, retrieving means and displaying means in such a manner that one or more case and clinical images are retrieved out of the case images and clinical images stored in said storing means and the retrieved case and clinical images are displayed.

BRIEF DESCRIPTION OF THE DRAWINGS

FIG. 1 is a block diagram showing one embodiment of the medical image filing apparatus according to the invention;

FIGS. 2A and 2B are schematic views respectively illustrating data constructions of a case index and a clinical index; and FIG. 3 is a flow chart for explaining an operation of the medical image filing apparatus shown in FIG. 1.

DESCRIPTION OF THE PREFERRED EMBODIMENTS

FIG. 1 is a block diagram showing one embodiment of the medical image filing apparatus according to the invention. In this embodiment, the medical image filing apparatus comprises a CPU 1, a keyboard 2, a retrieval device 3, a memory unit 4, an optical disc unit 5, a floppy disk unit 6, a printer 7 and a display unit 8. On a part of an optical disc of the optical disc unit 5 for example on hundreds of innermost tracks thereof have been previously recorded case images by means of a stamper at the time of manufacturing the optical disc. In addition, retrieval information i.e. case indexes of the previously recorded case images have been recorded on a floppy disc of the floppy disc unit 6. Further, clinical images such as endoscope images and X-ray images taken in clinical diagnoses are successively recorded on a non-recorded part of the optical disc under the control of the CPU 1. In addition, retrieval information i.e. clinical indexes of the recorded clinical images are recorded on the floppy disc by operating the keyboard 2 at the same time as the clinical image recording.

For example as shown in FIG. 2A, a case index includes retrieval data such as name of disease, age, part of disease and address data representing a filing position of the relevant case image in the optical disc. In addition, as shown in FIG. 2B, a clinical index is constructed by retrieval data including the same retrieval items as those of the case index such as patient ID, age, name of disease, part of disease, and address data representing a filing position of the relevant clinical image in the optical disc. These case indexes and clinical indexes are respectively recorded on different regions of the floppy disc.

In this embodiment, when a keyword representing at least one retrieval item corresponding to the desired clinical image is inputted from the keyboard 2, all the clinical indexes recorded on the floppy disc of the floppy disc unit 6 are collated with the inputted retrieval item by the retrieval device 3 under the control of the CPU 1 to obtain one or more clinical indexes having keywords idential with the inputted keyword. Then, the thus obtained clinical indexes are stored in the memory unit 4, and one or more desired clinical images recorded at the address positions in the optical disc of the optical disc unit 5 corresponding to the address data in the clinical indexes stored in the memory unit 4 are successively read out of the optical disc unit 5 and are displayed on the display unit 8 together with related retrieval data. In addition, the thus displayed clinical image and retrieval data are selectively outputted from the printer 7 by a command supplied from the keyboard 2. In this case, if there are many clinical indexes corresponding to the keyword supplied from the keyboard 2, the clinical indexes and the clinical images corresponding to the respective clinical indexes are displayed one by one on the display unit 8 in response to a command supplied from the keyboard 2. In the same manner, when a keyword representing the retrieval item corresponding to the desired case image is inputted from the keyboard 2, all the case indexes recorded on the floppy disc of the floppy disc unit 6 are collated with the inputted keyword by the retrieval device 3 to obtain one or more case indexes corresponding to the inputted keyword. Then, the thus obtained case indexes are stored in the memory unit 4, and desired case images recorded at the address positions in the optical disc of the optical disc unit 5 corresponding to the address data in the case indexes stored in the memory unit 4 are selectively read out of the optical disc unit 5 and are displayed on the display unit 8 together with the relevant retrieval data. In addition, the thus displayed case images and retrieval data are selectively outputted from the printer 7 by commands supplied from the keyboard 2.

Moreover, in this embodiment, the retrieved clinical image and case image are displayed simultaneously on the display unit 8. To this end, the display unit 8 may have two CRTs, or the clinical image and the case image may be displayed on respective half portions of a screen of a single CRT. It should be noted that clinical image and case image may be displayed on the CRT successively. Moreover, the memory unit 4 further comprises a clinical index memory 4a for storing the retrieved clinical indexes, a case index memory 4b for storing the retrieved case indexes, and an image memory 4c for storing one of these clinical and case images to be displayed on the display unit 8 next.

Further, in this embodiment, when the retrieval operation of the case image is effected after a clinical image has been retrieved and displayed, it is possible to retrieve automatically one or more case indexes having the retrieval data corresponding to that of said clinical image without inputting the keyword of the case image from the keyboard 2, and to display desired case images on the display unit 8.

Hereinafter, an operation of the medical image filing apparatus shown in FIG. 1 will be explained with reference to a flow chart shown in FIG. 3.

At first, the retrieval operation of the clinical images will be explained. When a keyword corresponding to the retrieval item such as patient ID is inputted from the keyboard 2, all the clinical indexes recorded on the floppy disc of the floppy disc unit 6 are collated with the inputted keyword by the retrieval device 3 under the control of the CPU 1 to retrieve one or more clinical indexes corresponding to the thus inputted keyword. Then, the clinical indexes thus obtained are stored in the clinical index memory 4a of the memory unit 4 and the clinical images having the clinical indexes thus extracted are displayed on the display unit 8. In this case, if the number of the retrieved clinical image is one, then a command representing whether the retrieval operation of the case image is necessary or not or a command whether the retrieval operation of another clinial image is necessary or not is inputted from the keyboard 2. Further, if the retrieval operation of the clinical image is effected again without retrieving the case images, the same operation as mentioned above is repeated. If the clinical and case images are not retrieved, the retrieval operation is ended. Moreover, if the retrieval operation of the case image is to be effected continuously, the clinical image displayed on the display unit 8 is stored in the image memory 4c of the memory unit 4 from the optical disc of the optical disc unit 5 and the retrieval operation of the case image is started in the manner mentioned below.

Contrary to this, if the number of the retrieved clinical image is a few, the retrieved clinical images are successively displayed on the display unit 8 by means of commands supplied from the keyboard 2 until a desired clinical image is displayed. Then, as is the same as the operations mentioned above, a command representing whether the retrieval operation of the case image is necessary or not or a command denoting whether the retrieval operation of the clinical image is necessary or not is inputted from the keyboard 2.

When the retrieval operation of the case image is effected after the end of the retrieval operation of the clinical image, the clinical image stored in the image memory 4c of the memory unit 4 is displayed on the display unit 8, and the case keyword corresponding to the desired case image is determined with reference to the displayed clinical image. In this case, the case keyword may be automatically set on the basis of the retrieval data of the clinical image previously retrieved and displayed on the display unit 8 by a single operation of the keyboard 2. Further, the case keyword may be set by inputting the keyword of the retrieval item corresponding to the desired case image from the keyboard 2 irregardless of the retrieval data of the displayed clinical image.

When the case keyword is determined, all the case indexes stored in the floppy disc of the floppy disc unit 6 are collated with the case keyword by the retrieval device 3 under the control of the CPU 1 to obtain one or more case indexes having the determined case keyword. The thus obtained case indexes are stored in the case index memory 4b of the memory unit 4, and the case images corresponding to the thus obtained case indexes are displayed on the display unit 8. In this case, if a plurality of case images are retrieved, these case images are successively displayed on the display unit 8 one by one by means of a command supplied from the keyboard 2. If the desired case image is displayed and there is only one retrieved case image, an operation such as retrieval end, retrieval for next case image and retrieval for next clinical image is selected by a command supplied from the keyboard 2. When the retrieval end operation is selected, all the operations are finished. When the retrieval operation for the next case image is selected, the case keyword of the case image to be retrieved is re-determined, and the retrieval operation of the thus determined case image is effected. When the retrieval operation of the next clinical image is selected, the keyword of the clinical image to be retrieved is inputted from the keyboard 2 to effect the retrieval operation of the clinical image. When the retrieval operation for the next case image is selected, the setting operation of the case keyword of the case image is performed by inputting the keyword of the retrieval item corresponding to the desired case image from the keyboard 2 irregardless of the retrieval data of the clinical image displayed on the display unit 8.

Moreover, the retrieved clinical image and the retrieved case image can be selectively outputted from the printer 7 by the command supplied from the keyboard 2.

In this manner, since the clinical image and the case image are recorded on the optical disc of the optical disc unit 5 and the desired clinical image and the case image corresponding thereto are retrieved from the images stored in the optical disc of the optical disc unit 5 and are simultaneously displayed side by side on the display unit 8, it is possible to effect the diagnosis easily in an accurate and fast manner. Moreover, in case of retrieving the case image, since the case image can be automatically retrieved on the basis of the retrieval data of the clinical image displayed on the display unit 8 by the command supplied from the keyboard 2 without inputting the case keyword, it is possible to effect the retrieval operation of the case image rapidly by the easy operation.

The present invention is not limited to the embodiments mentioned above, but various modifications are possible. For example, in the embodiment mentioned above, the case image and the clinial image are stored in the optical disc, but it is possible to store them in another recording medium such as floppy disc, magnetic tape, magnetic drum, etc. Similarly, the case index and the clinical index may be stored in other recording medium such as optical disc, magnetic tape, magnetic drum, etc. instead of the floppy disc. Further, it is also possible to record the case image and the index thereof on one record medium, while the clinical image and the index thereof are stored on another record medium. In this case, since the desired image can be independently read out of respective record mediums, it is possible to eliminate the image memory 4c. Moreover, the case image, the case index, the clinical image and the clinical index may be recorded on one common record medium. Further, if use is made of a plurality of image memories 4c, it is possible to store a plurality of retrieved images in the image memories 4c. In this case, it is possible to re-display the previously displayed image in an easy manner.

As mentioned above, according to the invention, since the case images as well as the clinical images are recorded on the optical disc and the case images are retrieved and displayed, it is possible to observe the case images in an easy and prompt manner. Therefore, the clinical image and the case image corresponding thereto can be displayed on the display unit 8 swiftly, and thus it is possible to effect an accurate diagnosis in a swift manner by comparing these displayed images with each other.

What is claimed is:

1. A medical image filing apparatus, comprising:

means for storing case images, clinical images taken in clinical diagnoses, case indexes including retrieval data for said case images, and clinical indexes including retrieval data for said clinical images;

means for inputting retrieval data corresponding to a desired one of said clinical images;

means for retrieving at least one image corresponding to said inputted retrieval data out of all the images stored in said storing means;

means for displaying retrieved images; and means for controlling said storing means, inputting means, retrieving means and displaying means in such a manner that one or more clinical images are first retrieved on the basis of inputted retrieval data and displayed on said displaying means and one or more case images are subsequently automatically retrieved on the basis of retrieval data corresponding to that of the clinical image displayed on said displaying means, thereby permitting retrieval and display of related clincal and case images for comparative diagnostic purposes.

2. A medical image filing apparatus according to claim 1, wherein said case image and said clinical image are simultaneously displayed on said display means.

3. A medical image filing apparatus according to claim 1, further comprising a printer for obtaining a hard copy.

4. A medical image filing apparatus according to claim 1, wherein said storing means comprises an optical disc unit for storing said case images and said clinical images in an optical disc, a floppy disc unit for storing said case indexes and said clinical indexes in a floppy disc, and a memory unit for storing at least one retrieved case index, and at least one retrieved clinical index.

5. A medical image filing apparatus according to claim 4, wherein said storing means further comprises an image memory for storing at least one retrieved image.

6. A medical image filing apparatus according to claim 5, wherein said image memory stores a plurality of retrieved images to be displayed successively on said displaying means.

7. A medical image filing apparatus according to claim 1, wherein said storing means comprises a first record medium for storing said case images and the case indexes corresponding thereto, and a second record medium for storing said clinical images and the clinical indexes corresponding thereto.

8. A medical image filing apparatus according to claim 1, wherein said storing means comprises a single record medium for storing said case images, said clinical images, said case indexes and said clinical indexes.

9. A medical image filing apparatus according to claim 1, wherein said inputting means comprises a keyboard.

* * * * *